US00PP18104P2

(12) United States Plant Patent
Olesen et al.

(10) Patent No.: US PP18,104 P2
(45) Date of Patent: Oct. 2, 2007

(54) ***CLEMATIS* PLANT NAMED 'EVIPO037'**

(50) Latin Name: *Clematis viticella*
Varietal Denomination: Evipo037

(75) Inventors: Mogens N. Olesen, Fredensborg (DK); Raymond Evison, St. Sampsons (GB)

(73) Assignees: Poulsen Roser A/S, Fredensborg (DK); Raymond J. Evison Ltd., Guernsey (GB)

( * ) Notice: Subject to any disclaimer, the term of this patent is extended or adjusted under 35 U.S.C. 154(b) by 0 days.

(21) Appl. No.: 11/418,418

(22) Filed: May 3, 2006

(51) Int. Cl.
*A01H 5/00* (2006.01)

(52) U.S. Cl. ..... Plt./228
(58) Field of Classification Search ..... Plt./228
See application file for complete search history.

*Primary Examiner*—Kent Bell
*Assistant Examiner*—June Hwu

(57) ABSTRACT

A new *Clematis* plant with a compact growth habit, profuse, violet-blue flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

2 Drawing Sheets

Botanical classification: Genus: *Clematis*. Species: *viticella*.
Variety denomination: 'Evipo037'.

SUMMARY OF THE CLAIMED PLANT

The present invention constitutes a new and distinct variety of *Clematis* plant which originated from a chance pollination of the female seed parent, an un-named seedling and an unknown male pollen parent.

The change pollination occurred during the summer of 1997 and the resulting seeds were planted the following winter in a controlled environment in Guernsey, Channel Islands. The new variety named 'Evipo037' originated as a single seedling from the stated chance pollination.

The new *clematis* plant may be distinguished from its female seed parent by the following combination of characteristics:

1. The claimed plant is more compact in growth habit than the seed parent.
2. The claimed plant has improved repeat flowering habit over the seed parent.

The objective of the hybridization of this *clematis* plant was to create a new and distinct variety for nursery culture with unique qualities such as:

1. Uniform and abundant violet-blue flowers;
2. Vigorous and compact growth, making the variety suitable for container culture; and
3. Improved disease resistance;
4. Improved repeat flowering characteristics.

This combination of qualities was lacking in *clematis* plants that were in commercial cultivation and the qualities have been substantially achieved in the new variety.

'Evipo037' was selected by Mogens N. Olesen and Raymond J. Evison in their *clematis* development program in the Channel Islands, United Kingdom in 1998. Asexual reproduction of 'Evipo037' by means of vegetative cuttings and traditional layering was first performed by Mogens N. Olesen and Raymond J. Evison in the nursery during the summer of 1998. This initial and subsequent asexual propagations have demonstrated that the characteristics of 'Evipo037' are true to type and are transmitted from one generation to the next.

BRIEF DESCRIPTION OF THE DRAWING

The accompanying color illustration show as true as is reasonably possible to obtain in color photographs of this type.

DETAILED DESCRIPTION OF THE VARIETY

Figure 1:
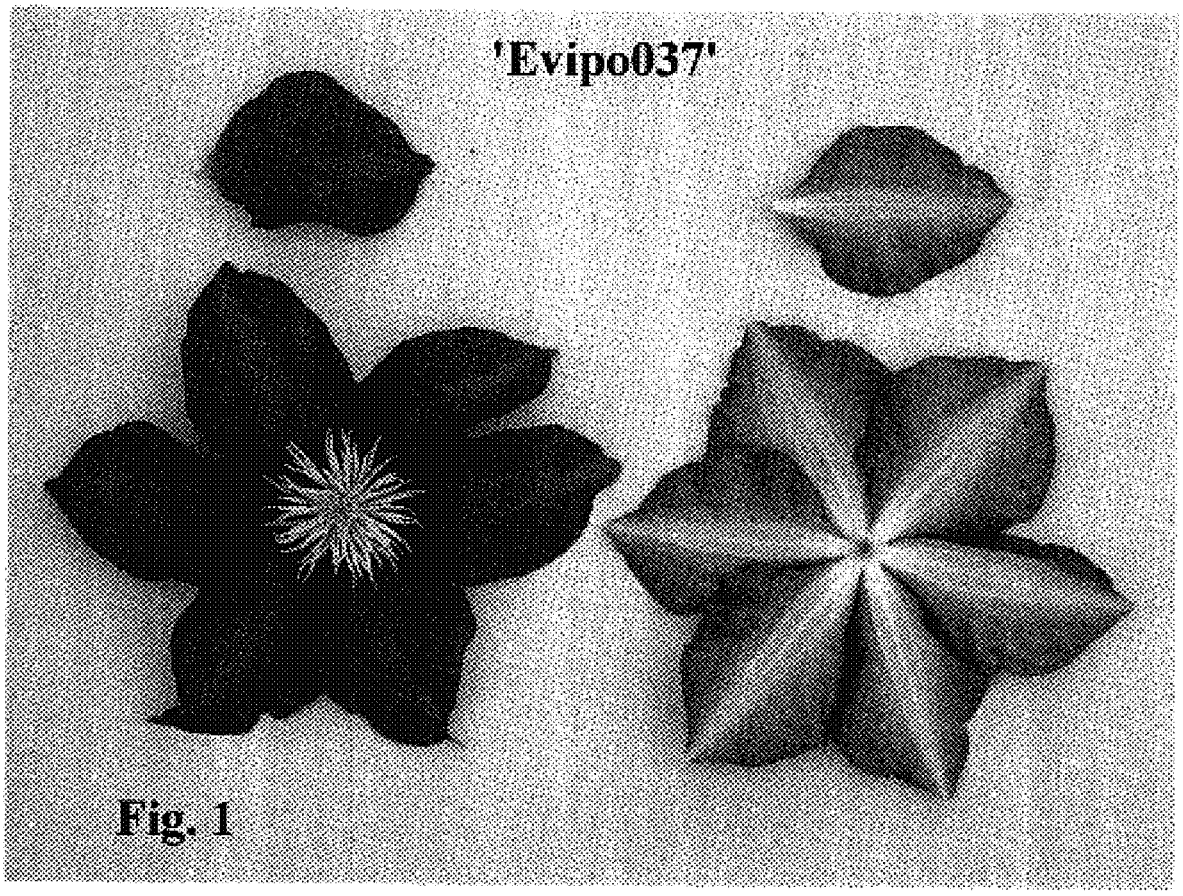
FIG. 1 Open flowers, upper and undersurface.
Figures 2A, 2B, 2C:
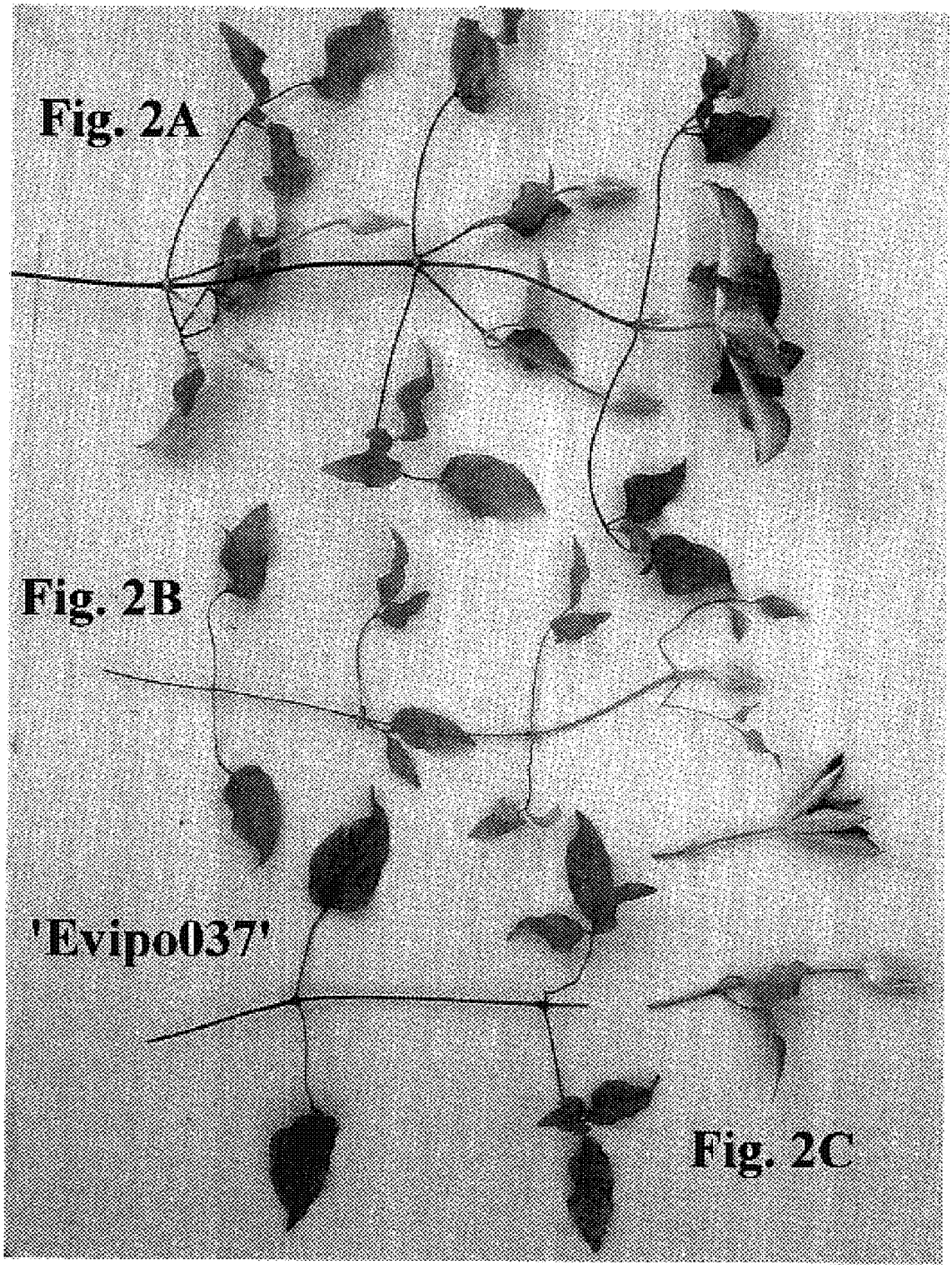
FIG. 2A Portion of the vine, in flower.
FIG. 2B Juvenile growth.
FIG. 2C Flower bud at various stages of development and mature leaves attached to vine.

The following is a detailed description of 'Evipo037', as observed in its growth throughout the flowering period in glasshouses in the Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety H. F. Young, a non patented *clematis* variety, are compared to 'Evipo037' in Chart 1.

CHART 1

| | 'Evipo037' | H.F. Young |
|---|---|---|
| Flower diameter | 130 to 150 mm | 150-185 mm |
| Tepal color, upper surface, upon opening | Violet-Blue N89C | Violet-Blue 92A |
| Tepal apex | mucronate | lanceolate |

FLOWER AND FLOWER BUD

Blooming habit: The natural flowering period is generally from May to June. Flowering normally occurs from October to November.

Flower bud:

*Size.*—Normally 30 to 50 mm in length. Bud diameter is 11 to 15 mm.

*Bud form.*—Ovate to elliptical.

*Bud color.*—Green Group 142B.

Peduncle:

*Surface texture.*—Smooth and lightly pubescent.

*Length.*—On average 52 to 65 mm.

*Color.*—Typically Green Group 142C.

*Strength.*—Moderately strong.

Receptacle: Absent.

Flower arrangement:

*Location on vine.*—New and old growth.

*Borne.*—Normally in clusters of 3 to 5 flowers.

Flower bloom:

*Size.*—On average, flowers are 130 to 150 mm in diameter and 30 mm in depth.

*Profile.*—Newly opened flowers are flat. After flowers have fully opened, tepals reflex and slightly twist.

*Fragrance.*—None.

*Lasting quality.*—Individual flowers normally remain on the plant for 7 to 12 days. Lasting quality of flowers after they have been removed from the plant is 3 to 5 days.

Tepals:

*Tepal color.*—Upon opening, the upper surface is uniformly Violet-Blue Group N89C. The lower surface is Violet-Blue Group 94D with a central bar colored Violet-Blue Group 92D, running the length of the tepal. The base of the tepal lower surface is White Group N155A. After opening, the upper surface is uniformly Violet-Blue Group N89D. At the point of attachment tepals are White Group N155A. The lower surface is Violet-Blue Group 94D with a central bar colored Violet-Blue Group 92D, running the length of the tepal. The base of the tepal lower surface is White Group N155A.

*Quantity.*—There are normally 6 to 7 tepals.

*Size.*—65 to 90 mm in length by 40 to 60 mm wide.

*Shape.*—Individual tepal shape broadly ovate. The tepal apex is mucronate. The tepal base is typically acute.

*Apex recurvature.*—Slightly recurved as the flower matures.

*Tepal cross section.*—New flowers are generally flat. As flowers mature, tepals begin to twist.

*Margins.*—Entire with moderately strong undulations.

*Persistence.*—Tepals drop off cleanly after flowers have matured.

Reproductive organs:

*Arrangement.*—Open.

*Pollen.*—Quantity: Moderate. Color: Yellow Group 4D.

*Anthers.*—Size: Normally 6 mm in length. Color: Yellow Group 6B. Quantity: 90 to 100.

*Filaments.*—Color: Violet-Blue Group 91B. Length: 9 to 15 mm.

*Pistils.*—Quantity: 50 to 60.

*Stigmas.*—As flowers fully mature, stigmas become superior in location relative to the length of the filaments and the height of the anthers.

*Styles.*—Color: Yellow Group 8D. Length: Normally 15 to 18 mm.

Seed head characteristics:

*Size.*—Seed heads are normally 40 mm in diameter. Individual seeds are 3 mm in diameter.

*Shape.*—The general shape of the individual seed is tear shaped with an elongated plumule.

PLANT

Plant form: Climbing.

Plant size: Seasons growth attains 1.2 to 1.5 meters in height. Average spread is 75 cm.

Hardiness: Trials to date show the variety hardy in USDA Zones 4–9.

Stem:

*Color.*—Juvenile stems are generally Greyed-Purple Group 183B. Mature stems are Greyed-Orange Group 175B.

*Internodes.*—On average, 110 to 170 mm between nodes.

*Dimensions.*—Normally 1 meter from the base of the plant to the flowering portion. Stems are normally 3 to 5 mm in diameter.

*Surface.*—Juvenile stems are smooth and lightly pubescent. Mature stems are generally ribbed.

Plant foliage:

*Leaf characteristics.*—Deciduous.

*Arrangement.*—Trifoliate, occasionally single.

*Leaf size.*—Compound leaves are normally 100 to 130 mm (l)×130 to 160 mm (w). Leaflets are normally 60 to 90 mm (l)×20 to 55 mm (w).

*Abundance.*—Generally, there are 14 leaves per 100 cm of stem.

*Leaf color.*—The upper surfaces of mature leaflets are Green Group 138A while the lower surfaces are Green Group 139D. Upper surfaces of juvenile leaflets are are Green Group 141B while the lower surfaces are Green Group 139C.

*Stipules.*—Absent.

*Petioles.*—Size: Normally 70 to 90 mm in length. Texture: Smooth. Color: Upper Greyed-Purple Group N186C. Lower surface is Yellow-Green Group 146D.

*Petioloule.*—Size: The terminal petioloule is normally 12 to 18 mm in length. Texture: Smooth. Color: Greyed-Purple Group N186C.

*Leaflet shape.*—Generally elliptic. The apex is acute. Base is rounded to cordate.

*Margin.*—Entire.

*Surface.*—The upper side is smooth.

*Thickness.*—Thin.

*Glossiness.*—New foliage is glossy. Mature leaves are matte.

Disease resistance: Subject to any disease that normally attacks the species. However the variety is more tolerant to *clematis* will than some *clematis.*

It is claimed:

1. We claim a new and distinct variety of *clematis* plant named 'Evipo037', substantially as described and illustrated, due to its abundant violet-blue flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo037'